United States Patent [19]

Antoku et al.

[11] Patent Number: 4,937,249
[45] Date of Patent: Jun. 26, 1990

[54] IMIDE DERIVATIVES AND THEIR PHARMACEUTICAL USE

[75] Inventors: Fujio Antoku, Takarazuka; Mayumi Yoshigi, Toyonaka; Ikutaro Saji, Suita; Kikuo Ishizumi, Toyonaka, all of Japan

[73] Assignee: Sumitomo Pharmaceuticals Company, Limited, Osaka, Japan

[21] Appl. No.: 262,575

[22] Filed: Oct. 25, 1988

[30] Foreign Application Priority Data

Oct. 26, 1987 [JP] Japan .................. 62-271462

[51] Int. Cl.$^5$ .................. A61K 31/445; C07D 413/14
[52] U.S. Cl. .................. 514/321; 514/278; 546/15; 546/16; 546/187; 546/198
[58] Field of Search ................ 514/321, 278; 546/198, 546/15

[56] References Cited

U.S. PATENT DOCUMENTS

| | | | |
|---|---|---|---|
| 4,186,203 | 1/1980 | Nunn et al. | 546/198 X |
| 4,352,811 | 10/1982 | Strupczewski et al. | 546/198 |
| 4,355,037 | 10/1982 | Strupczewski et al. | 546/198 |
| 4,390,544 | 6/1983 | Davis et al. | 546/198 X |
| 4,399,145 | 8/1983 | Graudoms et al. | 546/198 X |
| 4,408,053 | 10/1983 | Strupczewski et al. | 546/225 |
| 4,408,054 | 10/1983 | Strupczewski et al. | 546/226 |
| 4,411,901 | 10/1983 | Temple, Jr. et al. | 514/254 |
| 4,524,206 | 6/1985 | New et al. | 544/230 |
| 4,804,663 | 2/1989 | Kennis et al. | 514/258 |
| 4,812,461 | 3/1989 | Antoku et al. | 546/198 X |

OTHER PUBLICATIONS

Journal of Medicinal Chemistry, 1985, vol. 28, No. 6, p. 761-769.
Ch. Abs. 98:143397u., Strupczewski et al., 1983.
Ch. Abs. 102:203897v., Strupczewski et al., 1985.
Ch. Abs. 106:67292x., Kennis et al., 1987.

Primary Examiner—Mary C. Lee
Assistant Examiner—Bernard I. Dentz
Attorney, Agent, or Firm—Birch, Stewart, Kolasch & Birch

[57] ABSTRACT

A compound of the formula:

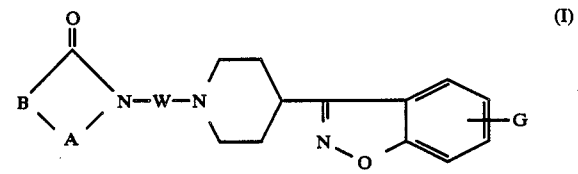

or its acid addition salt, which is useful as a psychotic drug.

11 Claims, No Drawings

IMIDE DERIVATIVES AND THEIR PHARMACEUTICAL USE

The present invention relates to imide derivatives, and their production and use. More particularly, it relates to novel imide derivatives and their salts, their production processes and their use as neuroleptic agents.

The imide derivatives of this invention are representable by the formula:

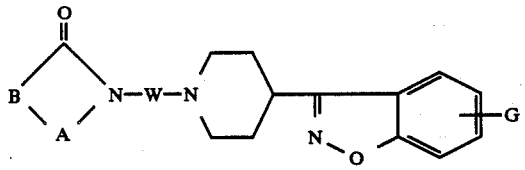

(I)

wherein
A is a carbonyl group or a sulfonyl group;
B is either one of the formulas:

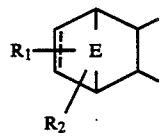

(in which $R_1$ and $R_2$ are each a hydrogen atom, or either one of them is a hydrogen atom and the other is a hydroxyl group, a lower alkyl group or a lower alkanoyloxy group, or $R_1$ and $R_2$ are combined together to represent an oxo group, E is a methylene group, an ethylene group or an oxygen atom and the full line accompanying a broken line ( ) indicates a single bond or a double bond),

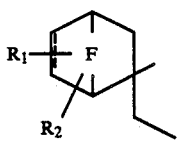

(in which F is a methylene group or an ethylene group and $R_1$, $R_2$ and the full line accompanying a broken line ( ) are each as defined above),

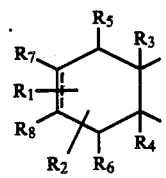

(in which $R_3$, $R_4$, $R_5$, $R_6$, $R_7$ and $R_8$ are each a hydrogen atom or a lower alkyl group and R1, R2 and the full line accompanying a broken line ( ) are each as defined above),

(in which $R_9$ and $R_{10}$ are each a lower alkyl group), or

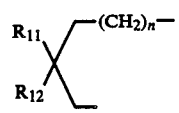

(in which $R_{11}$ and $R_{12}$ are each a lower alkyl group, or they are combined together to form a lower alkylene group and n is an integer of 0, 1 or 2) when A represents a carbonyl group,
or B is a 1,2-phenylene group when A represents a sulfonyl group;
W is a lower alkylene group, a lower alkenylene group, a lower alkynylene group or a lower alkylene group substituted with hydroxyl; and
G is a hydrogen atom, a lower alkyl group, a lower alkoxy group, a halogen atom or a hydroxyl group.

In the scope of this invention, there are included the salts of the imide derivatives (I), which include salts with organic or inorganic acids such as hydrochloric acid, hydrobromic acid, hydroiodic acid, sulfuric acid, acetic adid, óxalic acid, citric acid, malic acid, tartaric acid, fumaric acid and maleic acid. Conversion of these salts to their corresponding bases may be performed by a per se conventional manner such as treatment with an alkali.

In the above significances, the term "lower" is intended to mean a group having usually not more than 8 carbon atoms, preferably not more than 5 carbon atoms, unless otherwise indicated. Thus, the lower alkyl group may be a straight or branched one having 1 to 5 carbon atoms and covers methyl, ethyl, propyl, isopropyl, butyl, pentyl, etc. The lower alkanoyloxy group may be the one having 2 to 6 carbon atoms and includes acetoxy, propionyloxy, butyryloxy, etc. The lower alkylene group may be the one having 1 to 6 carbon atoms, and its examples are methylene, ethylene, trimethylene, propylene, tetramethylene, 2-methyltrimethylene, 2-methyltetramethylene, etc. The lower alkenylene group may be the one having 2 to 6 carbon atoms and covers ethenylene, propenylene, t-butenylene, 2-butenylene, etc. The lower alkynylene group is the one having 2 to 6 carbon atoms and includes 2-butynylene, 2-pentynylene, etc. The lower alkoxy group may be the one having 1 to 5 carbon atoms and can be, for instance, methoxy, ethoxy, propoxy, isopropoxy or butoxy. The term "halogen" includes fluorine, chlorine, bromine, iodine, etc.

As antipsychotic agents, particularly neuroleptics, there are known tricyclic compounds such as chlorpromazine (i.e. 2-chloro-10-(3-dimethylaminopropyl)-phenothiazine), butyrophenone compounds such as haloperidol (i.e. 4-[4-(4-chlorophenyl)-4-hydroxy-1-piperidinyl]-1-(4-fluorophenyl)-1-butanone), etc. These conventional neuroleptics are effective against positive symptoms such as hallucination and delusion but ineffective against negative symptoms such as autosynnoia and sentiment or volition torpor. Further, they produce serious side effects such as catalepsy and hypotension, which cause a great problem on their clinical use.

In recent years, some spiroimide compounds were developed as neuroleptics partly overcoming the drawbacks as seen in conventional neuroleptics. Their typical examples are buspirone (i.e. 8-[4-(2-pyrimidinyl)-1-piperazinylbutyl]-8-azaspiro[4,5]decane-7,9-dione) and tiaspirone (i.e. 8-[4-(3-benzisothiazolyl)-1-piperazinylbutyl]-8-azaspiro[4,5]decane-7,9-dione). These spiroimide compounds are alleviated in extrapyramidal side effects such as catalepsy inducing activity in comparison with butyrophenone compounds such as haloperidol. Further, for instance, tiaspirone is more potent than chlorpromazine and haloperidol in the efficacy against positive symptoms (when evaluated on anti-dopamine activity as measured by $D_2$ receptor binding assay). However, the anti-dopamine activity of tiaspirone drastically reduces on oral administration, and hence tiaspirone is still not sufficiently suitable for clinical use. Further, conventional antipsychotic agents including spiroimide compounds can exert only extremely weak efficacy against negative symptoms (when evaluated on anti-serotonin activity).

As a result of the extensive study, it has now been found that the imide derivatives (I) of the invention exhibit excellent neuroleptic activity. This invention is based on the above finding.

Accordingly, a main object of the present invention is to provide the imide derivatives (I) and their salts. Another obejct of this invention is to provide processes for production of the imide derivatives (I) and their salts. A further object of the invention is to provide the use of the imide derivatives (I) and their salts as antipsychotic drugs, particularly neuroleptics.

The imide derivatives (I) of the invention can be produced by various processes, of which typical examples are set forth below.

Process (A):

The imide derivative (I) is obtainable by either one of the following reactions:

rine, bromine, iodine), an alkylsulfonyloxy group (e.g. methanesulfonyloxy) or an arylsulfonyloxy group (e.g. p-toluenesulfonyloxy).

Namely, the imide derivative (I) can be produced by reacting the compound (II) with the amine (III) in an inert solvent (e.g. pyridine, n-butanol, benzene, toluene, xylene), preferably under reflux.

The imide derivative (I) can be also produced by reacting the compound (IV) with the compound (V) in an inert solvent (e.g. benzene, toluene, xylene, dimethylformamide, acetonitrile, n-butanol) in the presence of an acid binding agent such as an alkali or alkaline earth metal carbonate, bicarbonate or hydride (e.g. potassium carbonate, sodium bicarbonate, sodium hydride), a tertiary amine (e.g. triethylamine) or a pyridine base (e.g. pyridine), usually at room temperature or under heating.

The imide derivative (I) can be further produced by reacting the compound (VIII) with an amine (IX) in an inert solvent (e.g. benzene, toluene, xylene, dimethylformamide, acetonitrile, n-butanol) in the presence of an acid binding agent such as an alkali or alkaline earth metal carbonate, bicarbonate or hydride (e.g. potassium carbonate, sodium bicarbonate, sodium hydride), a tertiary amine (e.g. triethylamine) or a pyridine base (e.g. pyridine), usually at room temperature or under heating.

The starting compounds (II), (III), (IV), (V), (VIII) and (IX) are per se known or can be produced by known methods, of which some examples are shown below.

(i) Compound (II):

The compound (II) is described in the following literatures or obtainable by the methods as disclosed therein: Japanese Pat. Publn. (unexamined) No. 87262/1985; J.Am.Chem.Soc., 63, 3167 (1941); J.Am.Chem.Soc., 72, 1678 (1950); J.Am.Chem.Soc., 74, 3094 (1952); J.Am.Chem.Soc., 73, 4889 (1951); Justus Liebigs Annalen der Chemie, 514, 1 (1934), etc.

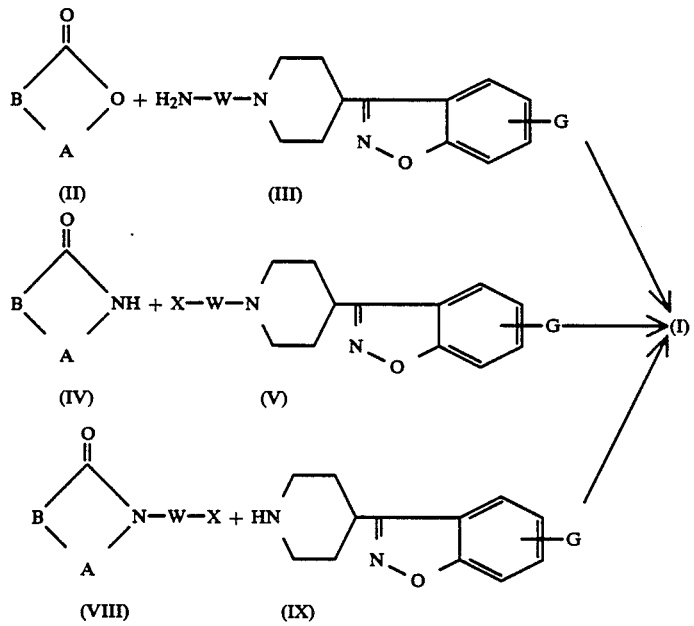

wherein A, B, G and W are each as defined above and X is a leaving group such as a halogen atom (e.g. chlo- (ii) Compounds (IV) and (VIII):

(III) and (V) are obtainable according to the following formulas:

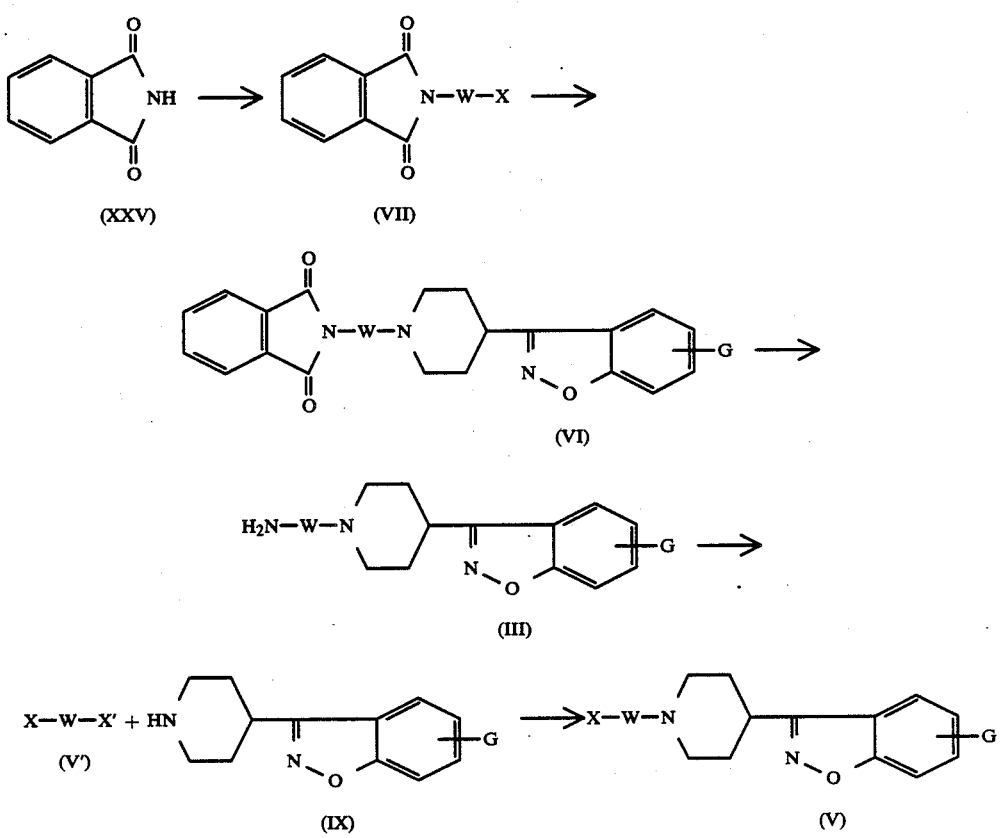

The compounds (IV) and (VIII) are obtainable according to the following formulas:

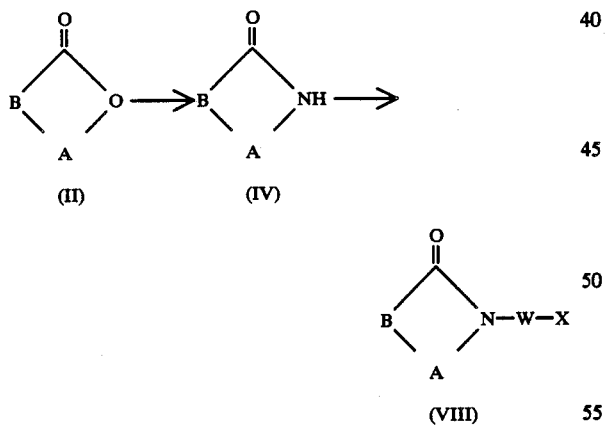

wherein A, B, W and X are each as defined above.

Namely, the compound (VIII) is produced from the compound (II) through the compound (IV) in a manner as described in EP-A-0109562, JP-A-87262/1985, JP-A-87284/1985, JP-A-23373/1985, etc. Compound (IV) and (VIII) are disclosed in the literatures recited above or obtainable by the method as described therein.

(iii) Compounds (III), (V) and (IX):

These compounds are know or can be prepared by known methods. For instance, the compound (IX) is disclosed in JP-A-90582/1983 or can be prepared by the method as described therein. Further, the compounds wherein G, W and X are each as defined above and X' is a leaving group such as a halogen atom, an alkylsulfonyloxy group (e.g. methanesulfonyloxy) or an arylsulfonyloxy group (e.g. p-toluenesulfonyloxy).

Namely, the compound (III) is obtainable by converting phthalimide (XXV) into the compound (VI) through the compound (VII) in a manner as disclosed in JP-A-87262/1985 and then subjecting the thus obtained compound (VI) to the Gabriel reaction. The compound (V) is obtainable by reacting the compound (V') with the compound (IX).

Process (B):

The imide derivative (I-1: W =lower alkylene) is obtainable by the following reaction:

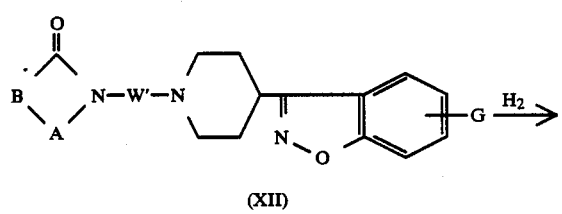

-continued

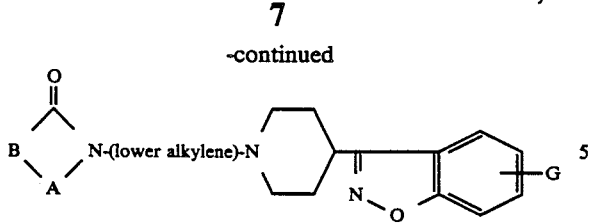

(I-1)

wherein A, B and G are each as defined above and W' is a lower alkenylene group or a lower alkynylene group.

Namely, the compound (I-1) is prepared by hydrogenation of the compound (XII). The hydrogenation may be achieved by any per se conventional procedure, particularly catalytic reduction. The catalytic reduction is usually carried out by treatment with hydrogen in the presence of a catalyst such as a metal (e.g. platinium, palladium, rhodium, nickel, cobalt), optionally deposited on a carrier such as carbon in an inert solvent (e.g. benzene, toluene, hexane, methanol, ethanol, ether, tetrahydrofuran, dioxane, ethyl acetate) at an ordinary temperature under an ordinary pressure. When desired, heating or cooling as well as elevation of pressure may be adopted for regulation of the reaction. After a theoretical amount of hydrogen is absorbed, the reaction mixture may be subjected to posttreatment in a conventional manner to recover the reaction product, which may be optionally purified.

The starting compound (XII) may be produced through Process (A) as hereinabove described or through Process (C) or (D) as hereinafter explained.

Process (C)

The imide derivative (I-2: W =—CH₂C≡CCH₂—) is obtainable by the following reaction:

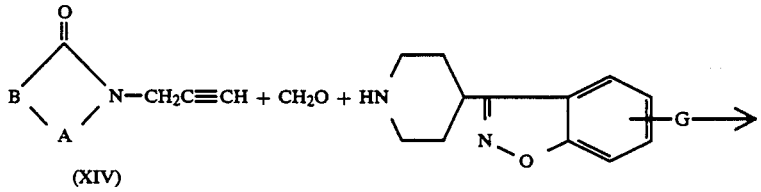

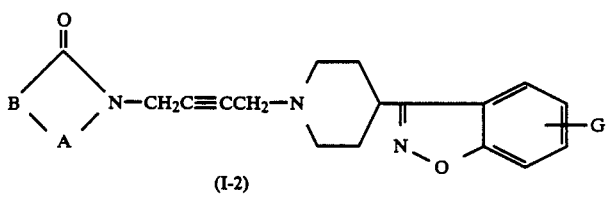

wherein A, B and G are each as defined above.

Namely, the N-propargyl derivative (XIV) is reacted with the piperazine derivative (IX) and formaldehyde in an inert solvent according to the Mannich reaction to give the compound (I-2). In the reaction system, the presence of a metallic ion as a catalyst is preferred to accomplish the reaction smoothly; a metal salt such as copper chloride, copper sulfate, copper acetate or iron chloride may be thus incorporated into the reaction system. Examples of the inert solvent are water, dioxane, tetrahydrofuran, ether, methylene glycol dimethyl ether, methyl cellosolve, etc. When desired, heating or cooling may be adopted for regulation of the reaction.

The starting compounds (XIV) and (IX) may be produced through Process (A) as hereinabove described.

Process (D):

The imide derivative (I-3: W =lower alkenylene) is obtainable by the following reaction:

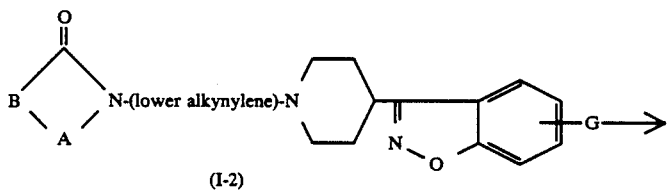

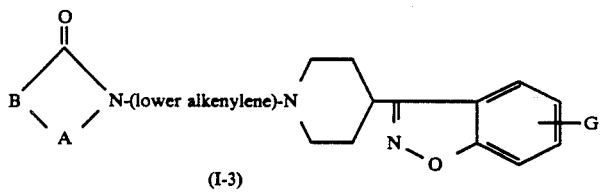

wherein A, B and G are each as defined above.

Namely, the compound (I-2) is subjected to hydrogenation, particularly catalytic hydrogenation to give the compound (I-3). The catalytic hydrogenation may be accomplished by treatment with hydrogen in the presence of a catalyst (e.g. platinium, palladium, rhodium, nickel, cobalt) in an inert solvent. For achievement of the hydrogenation partially, the use of a catalyst having a relatively weak activity such as palladium-calcium carbonate, palladium-barium sulfate or a Lindlar's catalyst, optionally poisoned with a basic amine, a sulfur compound or a lead compound is generally preferred. Examples of the inert solvent are benzene, toluene, hexane, methanol, ethanol, ether, tetrahydrofura, ethyl acetate, etc. The reaction can proceed well at an ordinary temperature under an ordinary pressure, but heating or cooling as well as elevation of pressure may be adopted for regulation of the reaction, if necessary. After absorption of hydrogen in a theoretical amount, the reaction is terminated, and the reaction mixture may be subjected to post-treatment by a conventional procedure.

The starting compound (I-2) is prepared by either Process (A) or (C).

Process (E):

The imide derivative (I-4 or I-4': W =hydroxysubstituted lower alkylene) is obtainable by either one of Procedure (1) or (2) as explained below.

wherein A, B and G are each as defined above.

The compound (I-4') is prepared by reacting the compound (IV) with the amine (XIX) in an inert solvent in the presence of a base, usually at a room temperature or while heating. Examples of the inert solvent are benzene, toluene, xylene, dimethylformamide, acetonitrile, n-butanol, etc. As the base, there may be used an alkali or alkaline earth metal carbonate, bicarbonate or hydride (e.g. potassium carbonate, sodium bicarbonate, sodium hydride), a tertiary amine (e.g. triethylamine), a pyridine base (e.g. pyridine) or the like.

The starting compounds (IV) and (XIX) may be produced by Process (A).

As stated above, the imide derivatives (I) of the invention exert a significant neuroleptic activity against positive and negative symptoms. Yet, they are very weak in side effects, particularly extrapyramidal side effects, as observed on conventional neuroleptic drugs of butyrophenone series and phenothiazine series. In addition, it may be noted that the neuroleptic activity of conventional spiroimide compounds on positive symptoms is remarkably reduced when administered orally, while that of the imide derivatives (I) is kept significant even when administered orally.

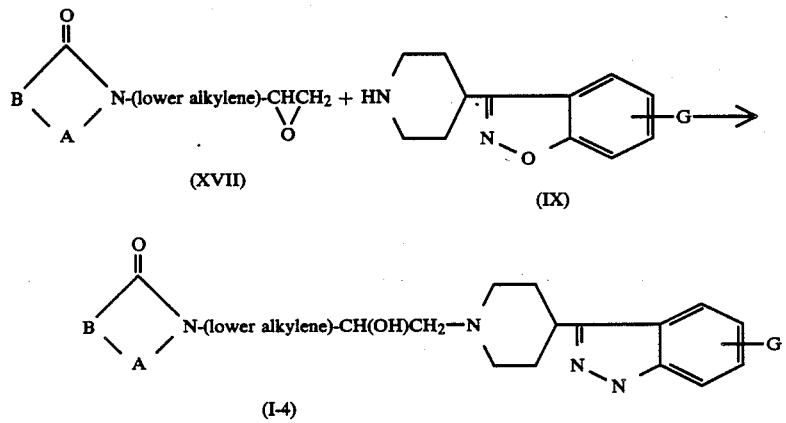

wherein A, B and G are each as defined above.

Namely, the epoxide (XVII) is reacted with the amine (IX) in an inert solvent, preferably under reflux, to give the compound (I-4). As the inert solvent, there may be exemplified benzene, toluene, xylene, dimethylformamide, acetonitrile, n-butanol, etc.

The starting compounds (XVII) and (IX) can be synthesized in the manner as described in Process A.

The above facts are well evidenced by the pharmacological test data as set forth below.

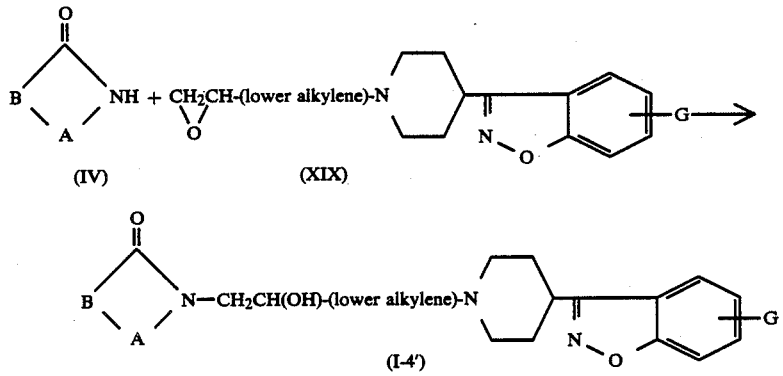

(I) Neuroleptic activity against positive symptoms:

(i) Anti-climbing activity

This activity was examined through the anticlimbing behavior test, i.e. the test for suppressing the climbing behavior induced by apomorphine in mice. A designed amount of the test compound was orally administered to several groups of dd strain male mice (bodyweight, 20 to 25 g; one group, 5 mice), and each of the animals was charged in an individual column cage of 12 cm in diameter and 14 cm in height having metal poles (each pole, 2 mm in diameter) vertically installed and arranged along the periphery with intervals of 1 cm. After 50 minutes, apomorphine (1.0 mg/kg) was subcutaneously injected, and 10 minutes after the injection, the behavior was observed during 10 minutes. Evaluation was made on the basis of the following criteria [P. Protais et al.: Psychopharmacology, 50, 1 - 6 (1976)]:

| Score | Evaluation |
| --- | --- |
| 0 | All the paws were on the floor |
| 1 | Only forepaws seized the pole of the cage |
| 2 | All the paws seized the pole of the cage; climbing behavior observed discontinuously |
| 3 | Continuous climbing behavior observed |

Climbing behavior control percentage per each dose was calculated by the following equation, and $ED_{50}$ (50% effective dose) was determined thereon:

$$\text{Control percentage (\%)} = \frac{\left(\text{Total score in control group}\right) - \left(\text{Total score in tested group}\right)}{\text{Total score in control group}} \times 100$$

The results are shown in Table 1.

(ii) Dopamine $D_2$ receptor binding assay

This assay was to examined a hydrophylic nature of the test compound to dopamine $D_2$ receptor in membrane fractions of corpus striatum taken out from bovine brain according to the method as described in T. Kuno et al: J.Neurochem., 41, 841 (1983).

(a) Preparation of membrane fractions:

Fresh corpus striatum taken out from bovine brain was homogenized in a 20-fold dilution of Tris-HCl buffer solution (pH, 7.4; 0.05 M) and centrifuged (50,000×g) for 10 minutes to give the membrane fractions, which were washed with the same volume of the buffer solution twice to give the membrane fractions for assay.

(ii) Displacement assay:

The membrane fractions as above obtained (containing 1 mg of protein) were incubated at 37° C. for 30 minutes in a buffer solution comprising [$^3$H] spiperone (19 Ci/mmol; 1 nM), sodium chloride (120 mM), Tris-HCl (pH, 7.4; 25 mM) and the test compound ($10^{-9}$ to $10^{-5}$ M) Upon termination of the reaction, the membrane fractions were collected through a Whatman GF/B glass filter and number of [$^3$H] spiperone bound with membrane was calculated by the aid of a liquid scintillation counter. Number of bindings specific to the $D_2$ receptor in [$^3$H] spiperone in a designed concentration of the test compound was measured according to the following equation and the $IC_{50}$ and $Ki$ was determined thereon on the basis of a hill plot:

Number of specific binding = (Total number of bindings) −

(Number of non-specific bindings, e.g. number of bindings in co-existence of $10^{-6}$ M spiperone)

l: concentration of [$^3$H] spiperone on assay
$K_D$: dissociation constant of [$^3$H] spiperone
The results are shown in Table 1.

TABLE 1

| Compound | Ki (nM) | $ED_{50}$ mg/kg (p.o.) | |
| --- | --- | --- | --- |
| | | 1 hr | 4 hrs |
| Compound obtained in Example 1 | 0.37 | 0.92 | 2.3 |
| Chlorpromazine | 29 | 1.8 | 8.8 |
| Tiaspirone | 0.5 | 9.4 | 61.5 |

(II) Neuroleptic activity against negative symptoms:

(i) Anti-head twitching activity

It is known that the efficacy on the negative symptom can be evaluated through anti-5-hydroxytryptamine 2 (5-HT$_2$) activity. It is also known that 5-HT$_2$ receptors (i.e. sub-type of 5-HT receptors) are activated by a 5-HT agonist to induce head-twitching in mice (M. Nakamura et al: J.Pharm. Pharmac., 30, 254–256 (1978); ibid., 30, 56–58 (1978); F.C. Colpert et al: Neuropharmacol., 22, 993–1000 (1983); A.R. Green et al: Neuropharmacol., 22, 573–578 (1983)). Based on the above knowledges, test for measurement of head twitches in mice was carried out for evaluation of the anti-5-HT$_2$ activity.

Nialamide (30 mg/kg) was intraperitoneally administered to several groups of dd strain male mice (bodyweight, 20 to 29 g), followed by oral administration of the test compound one hour later 5-Methoxytryptamine (5-MT) (2.5 mg/kg) was further administered through the tail vein one hour later, and the mice were admitted in a plastic cage (12 cm×12 cm×18 cm) for observation of head twitches for 3 minutes. Control percentage of each dose of the test compound was calculated, and $ED_{50}$ (50% effective dose) was determined by the method as described in Litchfield-Wilcoxson's method (cf. J. Pharmacological Experimental Therapy, 96, 99 (1949)).

The results are shown in Table 2.

TABLE 2

| Compound | $ED_{50}$ mg/kg (p.o.) |
| --- | --- |
| Compound obtained in Example 1 | 0.3–1.0 |
| Tiaspirone | 4.0 |

From the results in Table 1, it is understood that the imide derivatives (I) of the invention exert a high and prolonged affinity to the dopamine $D_2$ acceptor as the indication of the positive symptoms in comparison with conventional neuroleptic agents. From the results in Table 2, it is apparent that the imide derivatives (I) can improve the negative symptoms. Namely, the imide derivatives (I) are effective in treating not only the positive symptoms but also the negative symptoms, whereas conventional neuroleptic agents are effective only in either one of them. Further, the imide derivatives (I) are more excellent than conventional neuroleptic agents of the same type in potency and prolongation.

In addition, it was revealed that the imide derivatives (I) are strong in the main effect and weak in the side effect. Namely, they produce significant anti-dopamine activity (as the indication of the positive symptoms) and anti-serotonin activity (as the indication of the negative symptoms) yet are weak in the following side actions: (1) extrapyramidal side action (e.g. catalepsy-inducing activity) is weak; (2) alpha-blocking activity is low so that orthostatic hypopiesis is produced with less frequency; and (3) anti-cholinergic activity in the central nervous system is very low so that senile dementia is not accelerated.

The imide derivatives (I) of the invention may be thus stated to be neuroleptic drugs having high selectivity and high safety. They are usable not only to ordinary patients in mental disorders but also to elderly patients who are apt to be affected by various side effects. Besides, it may be noted that some of the imide derivatives (I) show not only neuroleptic activity but also other useful pharmacological activities such as analgesic activity, anti-allergic activity and circulatory activity.

For therapeutic administration, the imide derivatives (I) or their salts may be used in the form of conventional pharmaceutical preparations such as tablets, capsules, syrups, suspensions, solutions, emulsions and suppositories. Depending upon their administration route such as oral administration, parenteral administration or rectal administration, an appropriate preparation form may be used. In order to make those preparations, the imide derivatives (I) may be combined, if necessary, with suitable additives such as carriers, diluents, fillers, binders and stabilizers. In case of injectionable preparations, pharmaceutically acceptable buffers, solubilizers, isotonizers, etc. may be incorporated therein.

While the dosage of the imide derivatives (I) is vary with the symptom, age and weight of the patient, the dosage form, the administration mode and the like, the imide derivatives (I) may be, in general, administered to adults in an amount of about 0.5 to 1000 mg, preferably of about 3 to 500 mg per day in a single dose or divided doses.

Practical and presently preferred embodiments for production of the imide derivatives (I) as well as the intermediary compounds thereto are illustratively shown in the following Examples and Reference Examples.

Production of the compound (II):

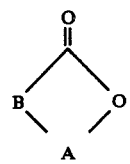

(II)

Reference Example 1 exo-5-Hydroxybicyclo[2.2.1]heptane-exo-cis-2,3-dicarboxylic acid:

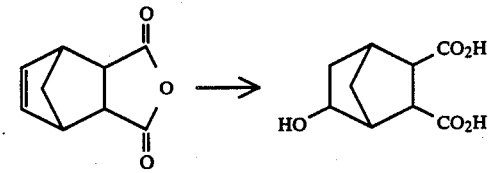

A suspension of bicyclo[2.2.1]hept-5-eneexo-2,3-dicarboxylic anhydride (3 g) in 50% aqueous sulfuric acid (30 ml) was stirred at 80° C for 3 hours and diluted with water (300 ml), followed by refluxing for 30 minutes. A slightly excess amount of aqueous barium chloride solution (a solution of barium chloride dihydrate (50 g) in water (200 ml)) was added thereto. After removal of the precipitated crystals by filtration, the filtrate was concentrated under reduced pressure. The residue was extracted with hot ethyl acetate (300 ml×2) and with hot acetone (300 ml×2). The extracts were combined together and concentrated under reduced pressure. The residual crystals were washed with acetonitrile to give the objective compound (1.09 g). Yield, 29.8%. M.P., 196 –198° C.

Reference Example 2 exo-5-Acetoxybicyclo[2.2.1]heptane-exo-2,3-dicarboxylic anhydride:

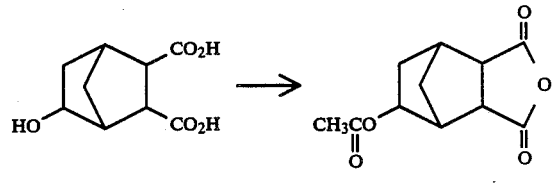

A mixture of exo-5-hydroxybicyclo[2.2.1]heptaneexo-2,3-dicarboxylic acid (3 g) and acetyl chloride (30 ml) was refluxed for 2 hours, followed by removal of acetyl chloride under reduced pressure The residue was combined with benzene, followed by distillation to give the objective compound as an oily substance.

Production of the compound (IV):

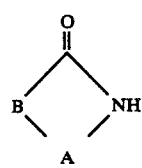

(IV)

Reference Example 3

Bicyclo[2.2.2]octane-2,3-dicarboximide:

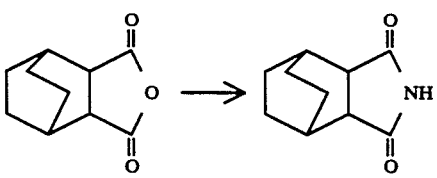

A solution of bicyclo[2.2.2]octane-2,3-dicarboxylic anhydride (3 g; 16.6 mmol) in tetrahydrofuran (9 ml) was dropwise added to a mixture of 29% aqueous ammonia (6 g; 83 mmol) and water (18 ml) while ice-cooling, and the resultant mixture was heated. After removal of the solvent by distillation under an ordinary pressure, acetic anhydride (10 ml) was added thereto, followed by refluxing for 30 minutes. The solvent was removed by distillation under reduced pressure, and the residue was combined with toluene (24 ml) and heated to dissolve. After cooling, the precipitated crystals were collected by filtration to give the objective compound. M.P., 199 –200° C.

Reference Example 4

Cyclohexane-1,2-dicarboximide:

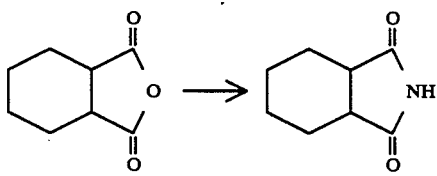

A mixture of cyclohexane-1,2-dicarboxylic anhydride (3 g; 19.5 mmol) and 29% aqueous ammonia (3.4 g) was heated to and kept at an inner temperature of 180 to 90 ° C. for 2 hours to give the objective compound quantitatively. M.P., 132 –136° C.

In the same manner as in Reference Example 3 or 4, the compounds as shown in Table 3 were obtained.

TABLE 3

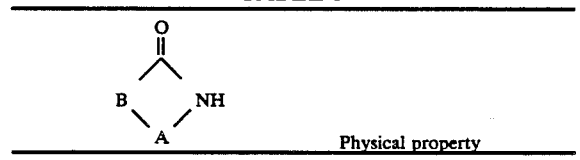

| | Physical property |
|---|---|
| 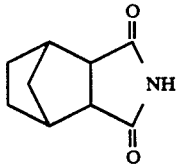 | M.P., 153–155° C. |
| 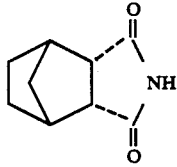 | M.P., 173–176° C. |

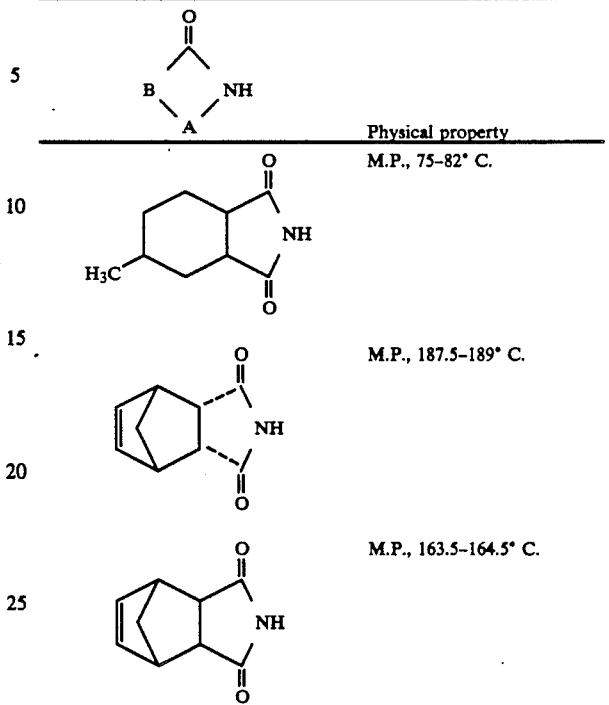

Production of the compound (VIII):

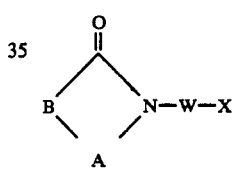

(VIII)

Reference Example 5

N-(4-Bromobutyl)bicyclo[2.2.1]heptane-2,3-di-exocarboximide:

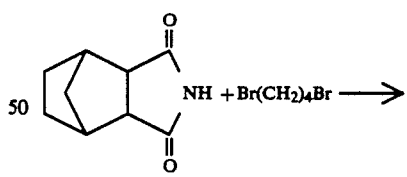

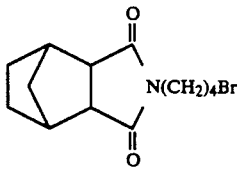

A mixture of bicyclo[2.2.1]heptane-2,3-di-exocarboximide (50 g), tetramethylene bromide (327 g), anhydrous potassium carbonate (50 g) and acetone (]b 500 ]l ml) was heated under the reflux for 5 hours while stirring, followed by cooling. After removal of insoluble materials by filtration, the filtrate was distilled under reduced pressure to give the objective compound as an oily substance (71.4 g). Yield, 78.6%. b.p., 173–180° C./0.04 mmHg.

IR $\nu_{max}^{film}$ (cm$^{-1}$): 1765, 1700, 1430, 1395.

Reference Example 6

N-(4-Bromobutyl)phthalimide:

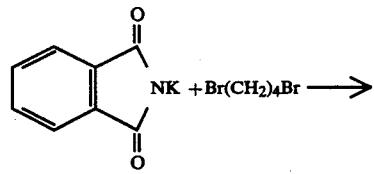 NK + Br(CH$_2$)$_4$Br ⟶

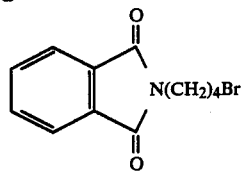

A mixture of phthalimide potassium salt (2 g; 10.8 mmol), 1,4-dibromobutane (10.8 g; 50 mmol) and dry dimethylformamide (10 ml) was stirred at a bath temperature of 90 to 100° C. for 10 hours. The precipitated crystals were removed by filtration, and the filtrate was concentrated under reduced pressure. Excess of 1,4-dibromobutane was removed by distillation, and the residue was purified by silica gel column chromatography to give the objective compound. M.P., 81–82° C.

In the same manner as in Reference Example 5 or 6, the compounds as shown in Table 4 were obtained.

TABLE 4

Structure: B–C(=O)–N(–W–X), with A connecting

| A | W | X | Physical property |
|---|---|---|---|
| norbornane-dicarboximide | —(CH$_2$)$_4$— | Br | IR $\nu_{max}^{film}$ (cm$^{-1}$): 1765, 1700 |
| norbornene-dicarboximide | —(CH$_2$)$_4$— | Br | IR $\nu_{max}^{film}$ (cm$^{-1}$): 1770, 1700 |
| norbornene-dicarboximide | —(CH$_2$)$_4$— | Br | b.p., 167–170° C./0.15 mmHg |
| cyclohexane-dicarboximide | —(CH$_2$)$_4$— | Br | IR $\nu_{max}^{film}$ (cm$^{-1}$): 1770, 1700 |

TABLE 4-continued $$\underset{A}{\overset{B}{\diagdown}}\underset{}{\overset{O}{\underset{\|}{C}}}\underset{}{\overset{}{\diagup}}N-W-X$$

| A | W | X | Physical property |
|---|---|---|---|
| 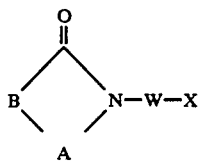 | —(CH$_2$)$_4$— | Br | IR $\nu_{max}^{film}$ (cm$^{-1}$): 1760, 1690 |
| 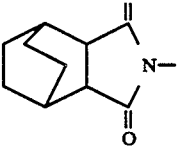 | —CH$_2$—C(H)=C(H)—CH$_2$— | Cl | IR $\nu_{max}^{film}$ (cm$^{-1}$): 1755, 1690 |
| 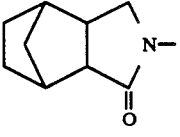 | —CH$_2$—C(H)=C(H)—CH$_2$— | Cl | IR $\nu_{max}^{film}$ (cm$^{-1}$): 1760, 1690 |
| 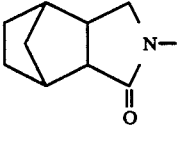 | —CH$_2$—C(H)=C(H)—CH$_2$— | Cl | IR $\nu_{max}^{film}$ (cm$^{-1}$): 1780, 1700 |
| 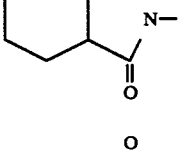 | —CH$_2$—C(H)=C(H)—CH$_2$— | Cl | IR $\nu_{max}^{film}$ (cm$^{-1}$): 1760, 1700 |
| 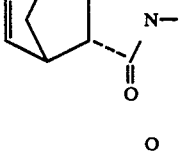 | —CH$_2$—C(H)=C(H)—CH$_2$— | Cl | IR $\nu_{max}^{film}$ (cm$^{-1}$): 1775, 1700 |
| 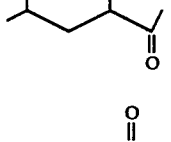 | —CH$_2$—C(H)=C(H)—CH$_2$— | Cl | IR $\nu_{max}^{film}$ (cm$^{-1}$): 1765, 1705 |

TABLE 4-continued

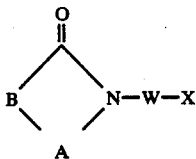

| A | W | X | Physical property |
|---|---|---|---|
| 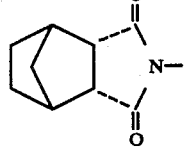 | $-CH_2-\underset{H}{\overset{H}{C}}=C-CH_2-$ | Cl | IR $\nu_{max}^{film}$ (cm$^{-1}$): 1760, 1700 |
| 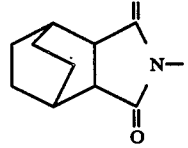 | $-CH_2-\underset{H}{\overset{H}{C}}=C-CH_2-$ | Cl | IR $\nu_{max}^{film}$ (cm$^{-1}$): 1760, 1685–1705 |
| 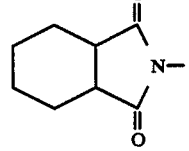 | $-CH_2-C\equiv C-CH_2-$ | Cl | IR $\nu_{max}^{film}$ (cm$^{-1}$): 1780, 1700–1720 |

Reference Example 7
N-(4-Bromo-3-hydroxybutyl)cyclohexane-1,2-dicarboximide:

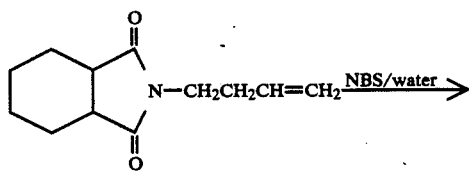

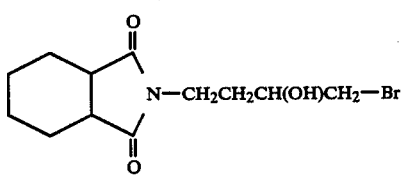

A mixture of N-(3-butenyl)cyclohexane-1,2-dicarboximide (1 g; 4.8 mmol), N-bromosuccinimide (0.86 g; 4.8 mmol) and water (2 ml) was stirred at room temperature for 4 hours. After completion of the reaction, water was added to the reaction mixture to dissolve insoluble materials, followed by extraction with benzene. The benzene extract was washed with a saturated aqueous sodium chloride solution, dried over magnesium sulfate and concentrated under reduced pressure to give the objective compound (1.4 g). Yield, 95.8%.

IR $\nu_{max}^{film}$ (cm$^{-1}$): 1760, 1700, 1440, 1400, 1360.

Production of the compound (XIV):

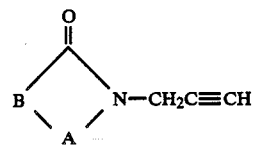

(XIV)

Reference Example 8
N-Propargylbicyclo[2.2.1]heptane-2,3-di-exocarboximide:

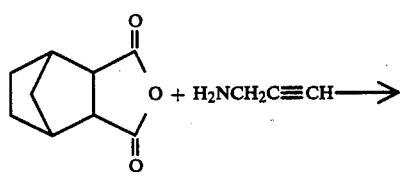

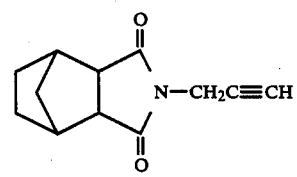

To a solution of propargylamine (1.12 g) in dry tetrahydrofuran (10 ml), a solution of bicyclo[2.2.1]-heptane-2,3-di-exo-carboxylic anhydride (1.64 g) in dry tetrahydrofuran (10 ml) was dropwise added at room temperature under stirring, and the resultant mixture was gradually heated to distill off the solvent and kept at an oily bath temperature of 150° C. for 30 minutes. The residue was purified by chromatography to give the objective compound.

Yield, 81%. M.P., 94 –94.5° C.

Reference Example 9

N-Propargylbicyclo[2.2.1]heptane-2,3-di-exocarboximide:

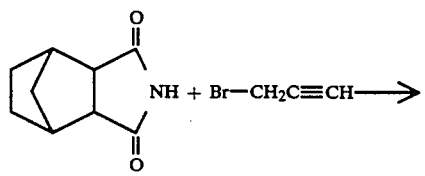

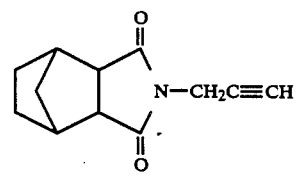

A solution of bicyclo[2.2.1]heptane-2,3-di-exocarboximide (3.30 g), propargyl bromide (2.62 g) and anhydrous potassium carbonate (3.32 g) in dry acetone (30 ml) was stirred under reflux for 1 hour in nitrogen atmosphere. After cooling, inorganic materials were removed by filtration, and the filtrate was concentrated under reduced pressure. The residue was combined with chloroform (20 ml) and n-hexane (20 ml), and insoluble materials were eliminated by filtration with celite. The filtrate was evaporated, and the residue was recrystallized from n-hexane to give the objective compound.

Yield, 91%. M.P., 94–94.5° C.

In the same manner as in Reference Example 8 or 9, the compounds as shown in Table 5 were obtained.

TABLE 5

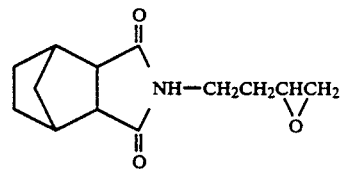

| A | Physical property |
|---|---|
| (norbornene structure) | M.P., 124–126° C. |

Production of the compound (SVII):

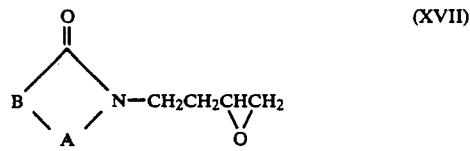

(XVII)

Reference Example 10

N-(3,4-Epoxybutyl)bicyclo[2.2.1]heptane-2,3-di-exo-carboximide:

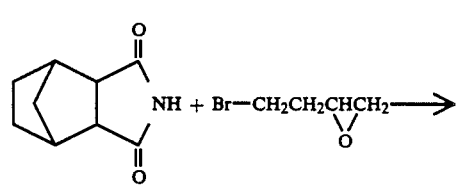

A mixture of bicyclo[2.2.1]heptane-2,3-di-exocarboximide (2.3 g; 14.2 mmol), 4-bromo-1,2-epoxybutane (2 g; 14.2 mmol), potassium carbonate (2.9 g; 21.3 mmol) and acetone (35 ml) was stirred for 8.5 hours under reflux. After completion of the reaction, the reaction mixture was cooled, and insoluble materials were removed by filtration. The filtrate was concentrated under reduced pressure. The residue was combined with toluene (100 ml), and the resulting mixture was shaken with a saturated aqueous sodium chloride solution (50 ml). The aqueous layer was reextracted with toluene (100 ml), and the toluene extract was combined with the organic layer, dried over magnesium sulfate and concentrated under reduced pressure. The residue was purified by silica gel column chromatography to give the objective compound (2.6 g).

Yield, 79.4%.

IR $\nu_{max}^{film}$ (cm$^{-1}$): 1765, 1700, 1480, 1440, 1400.

Reference Example 11

N-(3,4-Epoxybutyl)bicyclo[2.2.1]heptane-2,3-di-exo-carboximide:

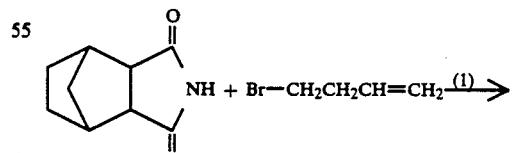

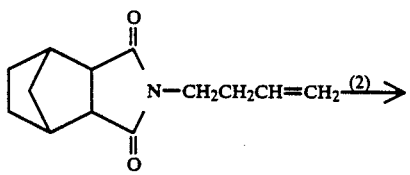

-continued

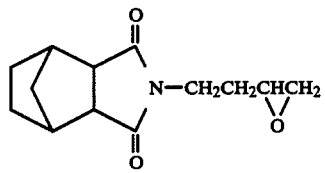

(1) To a mixture of bicyclo[2.2.1]heptane-2,3-diexo-carboximide (1.65 g) and dimethylformamide (5 ml), a solution of 4-bromo-1-butene (1.62 g) in dimethylformamide (3 ml) was added while stirring at room temperature, followed by addition of powdery anhydrous potassium carbonate (2.07 g) thereto. The resultant mixture was heated and allowed to react at an inner temperature of 90 to 100° C for 1 hour. The reaction mixture was combined with chloroform and subjected to filtration. The filtrate was concentrated under reduced pressure, combined with toluene, washed with water and dried. The solvent was removed under reduced pressure to give the objective compound (2.22 g) as an oily substance.

IR $\nu_{max}^{film}$ (cm$^{-1}$): 3050, 3000, 2925, 1485, 1440.

(2) To a solution of N-(3-butenyl)bicyclo[2.2.1]-heptane-2,3-di-exo-carboximide (2.05 g) in dichloromethane (15 ml), a solution of m-chloroperbenzoic acid (2.4 g) in dichloromethane (35 ml) was added while stirring at room temperature, and the resultant mixture was allowed to react for 15 hours. After completion of the reaction, the reaction mixture was treated with an aqueous solution of sodium thiosulfate, washed with an aqueous solution of sodium bicarbonate and dried. The solvent was distilled under reduced pressure, and the residue was purified by silica gel column chromatography to give the objective compound (2.03 g; 96.4%) as an oily substance.

IR $\nu_{max}^{film}$ (cm$^{-1}$): 1765, 1700, 1480, 1440, 1400.

In the same manner as in Reference Example 10 or 11, the compounds as shown in Table 6 were obtained.

TABLE 6

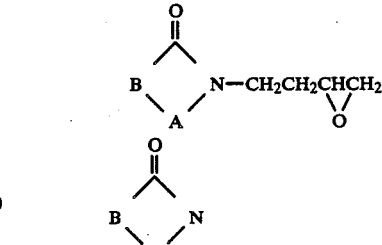

(XVII)

| Structure | Physical property |
|---|---|
| (norbornane imide) | IR $\nu_{max}^{film}$ (cm$^{-1}$): 1770, 1700, 1440, 1440 |
| (cyclohexane imide) | IR $\nu_{max}^{film}$ (cm$^{-1}$): 1775, 1710, 1445, 1405, 1355 |
| (methyl cyclohexane imide) | IR $\nu_{max}^{film}$ (cm$^{-1}$): 1765, 1700, 1440, 1395, 1350 |
| (norbornene imide) | IR $\nu_{max}^{film}$ (cm$^{-1}$): 1765, 1705, 1440, 1395, 1365 |
| (norbornene imide isomer) | IR $\nu_{max}^{film}$ (cm$^{-1}$): 1770, 1700, 1440, 1400, 1365 |
| (bicyclic NH imide) | IR $\nu_{max}^{film}$ (cm$^{-1}$): 1765, 1680, 1440, 1405, 1390 |

Production of the compound (I):

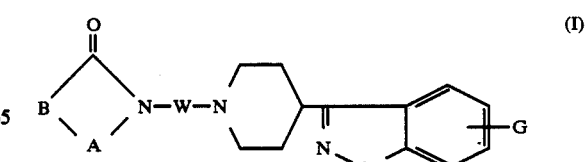

(I)

Example 1

N-[4-{4-(6-Fluoro-1,2-benzisoxazol-3-yl)piperidinyl}butyl]cyclohexane-1,2-dicarboximide:

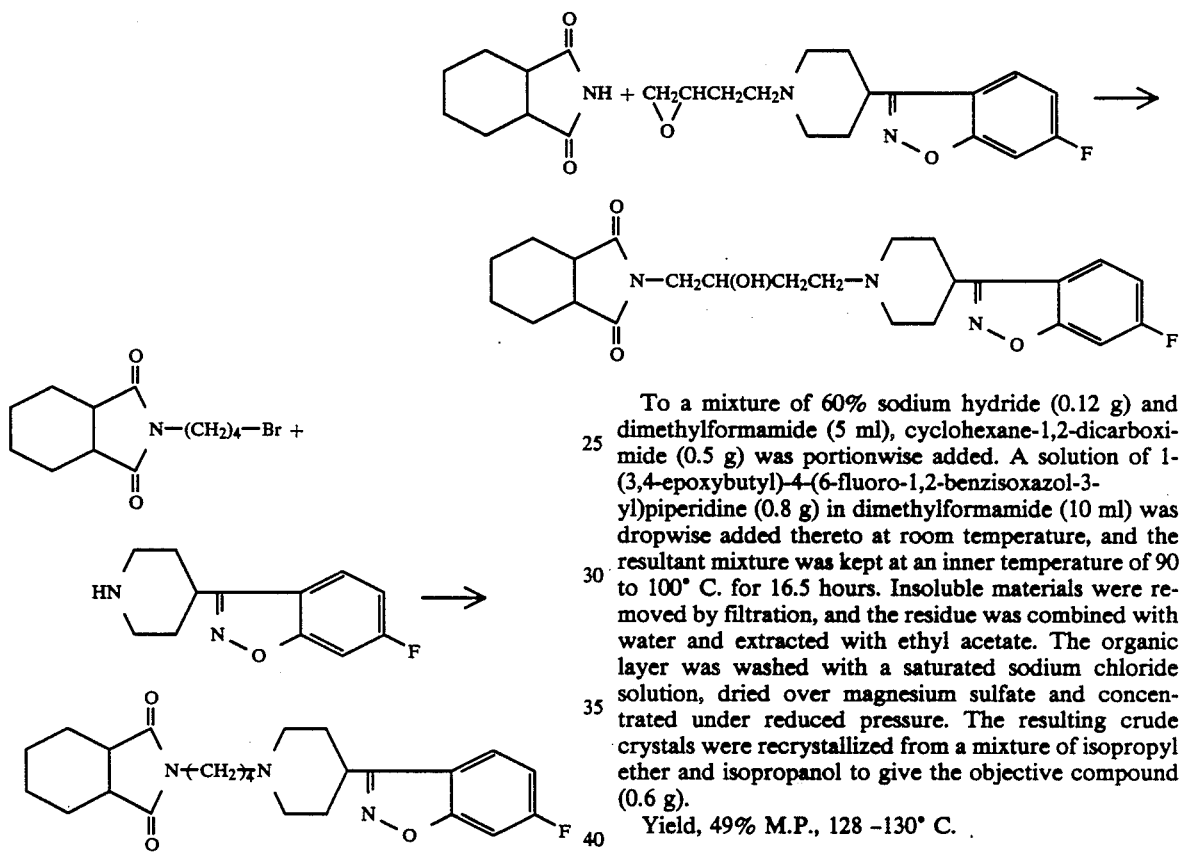

A mixture of N-(4-bromobutyl)cyclohexane-1,2-dicarboximide (2.36 g), 3-(4-piperidinyul)-6-fluoro-1,2-benzisoxazole (1.5 g), potassium carbonate (1.13 g), potassium iodide (0.13 g) and dimethylformamide (30 ml) was kept at a bath temperature of 90 to 100° C. for 11 hours. After removal of insoluble materials, the solvent was removed by distillation under reduced pressure. The residue was combined with water and extracted with chloroform. The chloroform extract was washed with a saturated sodium chloride solution, dried over magnesium sulfate and concentrated under reduced pressure. The residue was purified by silica gel chromatography, followed by treatment with hydrogen chloride to give the objective compound (2.3 g). Yield, 72.8%. M.P., 230 –231° C. (HCl salt).

Example 2

N-[4-{4-(6-Fluoro-1,2-benzisoxazol-3-yl)piperidinyl}-2-hydroxybutyl]cyclohexane-1,2-dicarboximide:

To a mixture of 60% sodium hydride (0.12 g) and dimethylformamide (5 ml), cyclohexane-1,2-dicarboximide (0.5 g) was portionwise added. A solution of 1-(3,4-epoxybutyl)-4-(6-fluoro-1,2-benzisoxazol-3-yl)piperidine (0.8 g) in dimethylformamide (10 ml) was dropwise added thereto at room temperature, and the resultant mixture was kept at an inner temperature of 90 to 100° C. for 16.5 hours. Insoluble materials were removed by filtration, and the residue was combined with water and extracted with ethyl acetate. The organic layer was washed with a saturated sodium chloride solution, dried over magnesium sulfate and concentrated under reduced pressure. The resulting crude crystals were recrystallized from a mixture of isopropyl ether and isopropanol to give the objective compound (0.6 g).

Yield, 49% M.P., 128 –130° C.

Example 3

N-[4-{4-(6-Fluoro-1,2-benzisoxazol-3-yl)piperidinyl}-3-hydroxybutyl]cyclohexane-1,2-dicarboximide:

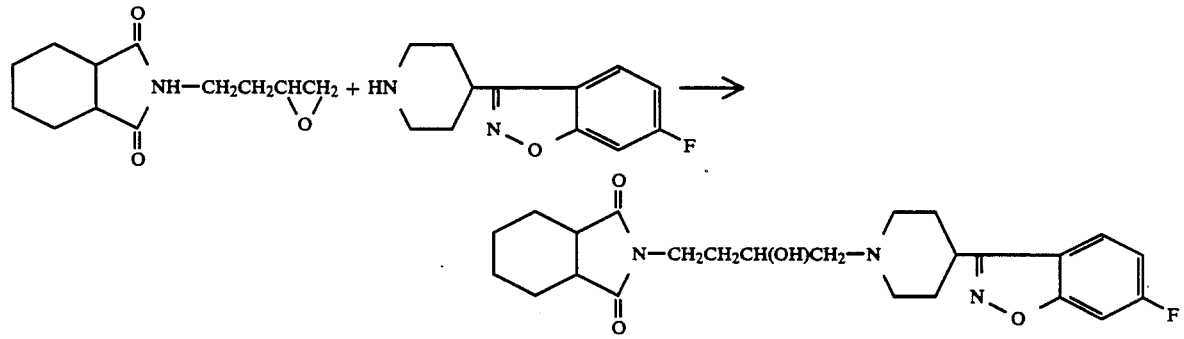

A mixture of N-(3,4-epoxybutyl)cyclohexane-1,2-dicarboximide (1.5 g), 3-(4-piperidinyl)-6-fluoro-1,2-benzisoxazole (1.5 g) and n-butanol (30 ml) was refluxed for 5.5 hours, followed by evaporation of n-butanol under reduced pressure. The residue was combined with isopropanol (100 ml) and then with active carbon (1.5 g), followed by stirring for 30 minutes. After removal of active carbon by filtration, the solvent was removed under reduced pressure. The residue was treated with hydrogen chloride to give the objective compound (1.4 g).

Yield, 42.9%. M.P., 223–225° C. (HCl salt).

Example 4

N-[4-(6-Fluoro-1,2-benzisoxazol-3-yl)piperidinylmethyl]cyclohexane-1,2-dicarboximide:

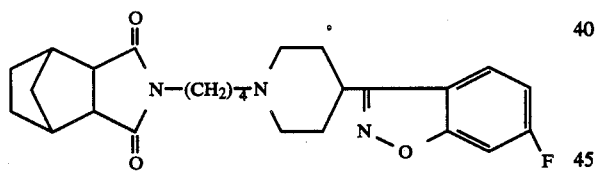

A mixture of cyclohexane-1,2-dicarboximide (1.48 g), 3-(4-piperidinyl)-6-fluoro-1,2-dibenzisoxazole (2 g), 35% aqueous formalin (0.83 g) and ethanol (25 ml) was refluxed for 17 hours. After removal of the solvent, the residue was purified by silica gel chromatography to give the objective compound (1.9 g).

Yield, 53.2%. M.P., 160–163° C. (HCl salt).

Example 5

In the same manner as in Example 1, 2, 3 or 4, there was obtained N-[4-{4-(6-fluoro-1,2-benzisoxazol-3-yl)-piperidinyl}butyl]bicyclo[2.2.1]heptane-2,3-di-exo-carboxyimide of the following formula:

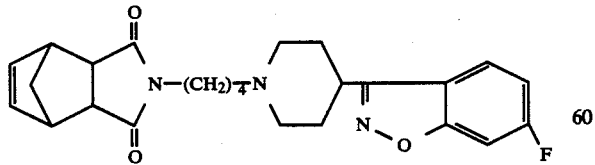

M.P., 252–253.5° C. (HCl salt).

Example 6

In the same manner as in Example 1, 2, 3 or 4, there was obtained N-[4-{4-(6-fluroro-1,2-benzisoxazol-3-yl)-piperidinyl}butyl]bicyclo[2.2.1]hept-5-en-2,3-di-exocarboximide of the following formula:

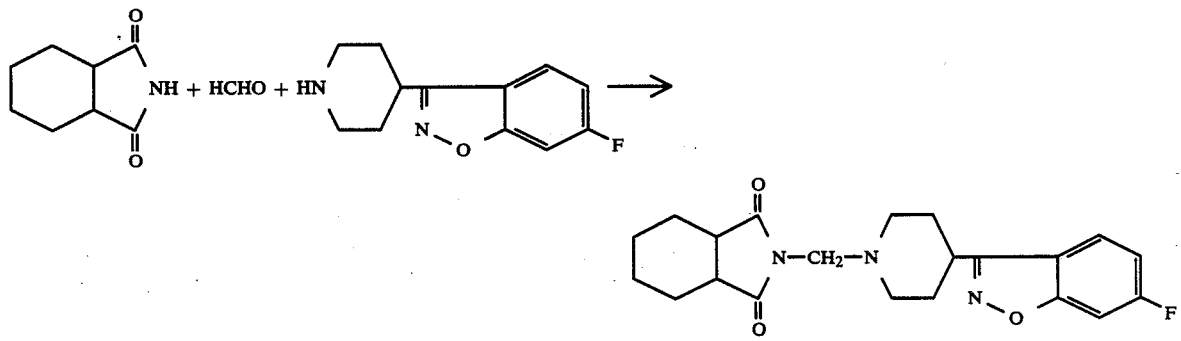

M.P., 231–232° C. (HCl salt).

Example 7

In the same manner as in Example 1, 2, 3 or 4, there was obtained N-[4-{4-(6-fluoro-1,2-benzisoxazol-3-yl)-piperidinyl}butyl]bicyclo[2.2.1]heptane-2,3-di-endo-carboximide of the following formula:

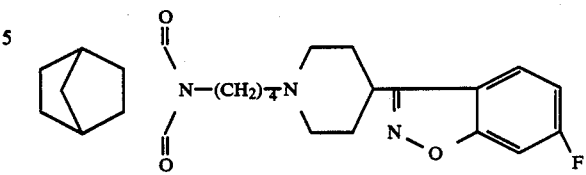

M.P., 219–221° C. (HCl salt).

Example 8

In the same manner as in Example 1, 2, 3 or 4, there was obtained N-[4-{4-(6-fluoro-1,2-benzisoxazol-3-yl)-piperidinyl}butyl]bicyclo[2.2.2]octane-2,3-di-carboximide of the following formula:

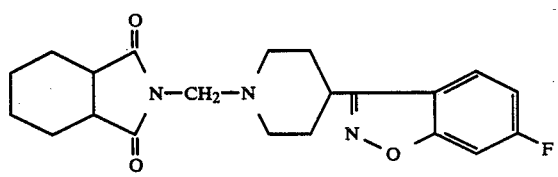

M.P., 237–238° C. (HCl salt).

Example 9

In the same manner as in Example 1, 2, 3 or 4, there was obtained 8-[4-{4-(6-fluoro-1,2-benzisoxazol-3-yl)-piperidinyl}butyl]-8-azaspiro[4.5]decane-7,9-dione of the following formula:

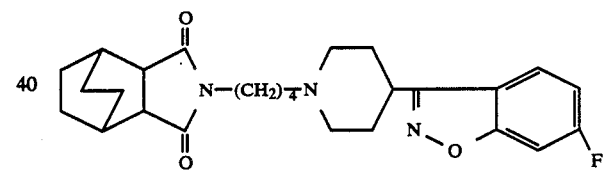

M.P., 204–205° C. (HCl salt).

Example 10

In the same manner as in Example 1, 2, 3 or 4, there was obtained N-[4-{4-(6-fluoro-1,2-benzisoxazol-3-yl)-piperidinyl}butyl]-7-oxabicyclo[2.2.1]heptane-2,3-di-exocarboximide of the following formula:

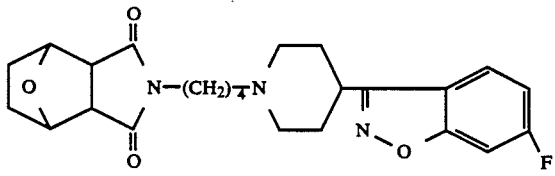

M.P., 240–242° C. (HCl salt).

Example 11

In the same manner as in Example 1, 2, 3 or 4, there was obtained N-[4-{4-(6-fluoro-1,2-benzisoxazol-3-yl)-piperidinyl}butyl]-4,4-dimethyl-2,6-piperidine-dione of the following formula:

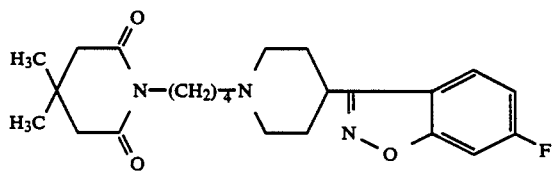

M.P., 221–223° C. (HCl salt).

Example 12

In the same manner as in Example 1, 2, 3 or 4, there was obtained N-[4-{4-(6-fluoro-1,2-benzisoxazol-3-yl)-piperidinyl}butyl]-1,2-benzisothiazol-3(2H)-one-1,1-dioxide of the following formula:

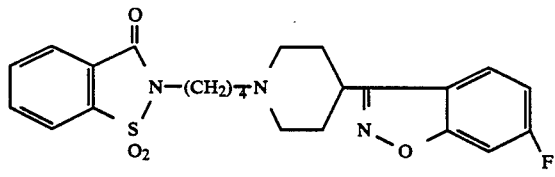

M.P., 235–236° C. (HCl salt).

Example 13

In the same manner as in Example 1, 2, 3 or 4, there was obtained N-[4-{4-(6-fluoro-1,2-benzisoxazol-3-yl)-piperidinyl}butyl]bicyclo[2.2.1]hept-5-en-2,3-di-endocarboximide of the following formula:

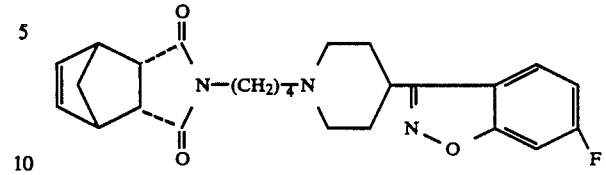

M.P., 191–193° C. (HCl salt).

Example 14

In the same manner as in Example 1, 2, 3 or 4, there was obtained N-[4-{4-(6-fluoro-1,2-benzisoxazol-3-yl)-piperidinyl}butyl]-4-cyclohexene-1,2-dicarboximide of the following formula:

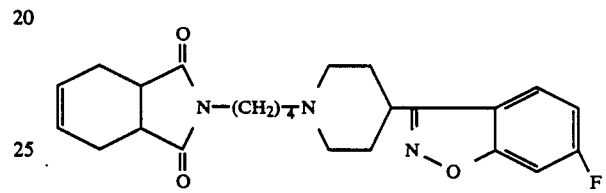

M.P., 217–218° C. (HCl salt).

Example 15

In the same manner as in Example 1, 2, 3 or 4, there was obtained N-[4-{4-(6-fluoro-1,2-benzisoxazol-3-yl)-piperidinyl}butyl]-4-methylcyclohexane-1,2-dicarboximide of the following formula:

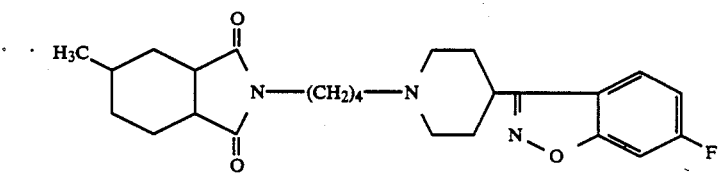

M.P., 200–201° C. (HCl salt).

Example 16

In the same manner as in Example 1, 2, 3 or 4, there was obtained N-[4-{4-(6-fluoro-1,2-benzisoxazol-3-yl)-piperidinyl}butyl]-4-methylcyclohexene-1,2-dicarboximide of the following formula:

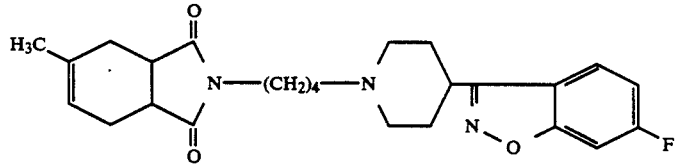

M.P., 188–190° C. (HCl salt).

Example 17

In the same manner as in Example 1, 2, 3 or 4, there was obtained N-[4-{4-(6-fluoro-1,2-benzisoxazol-3-yl)-piperidinyl} butyl]-3,3-dimethylcyclopropane-1,2-dicarboximide of the following formula:

piperidinyl }-2-trans-butenyl]bicyclo[2.2.1]heptane-2,3-diexo-carboximide of the following formula:

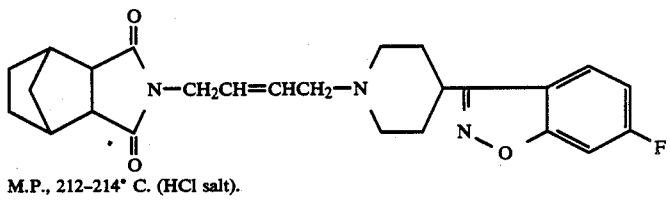

M.P., 212–214° C. (HCl salt).

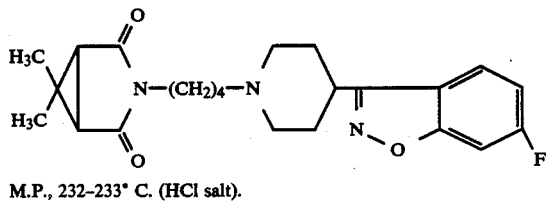

M.P., 232–233° C. (HCl salt).

Example 18

In the same manner as in Example 1, 2, 3 or 4, there was obtained N-[4-{4-(6-fluoro-1,2-benzisoxazol-3-yl)-piperidinyl}-2-trans-butenyl]cyclohexane-1,2-dicarboximide of the following formula:

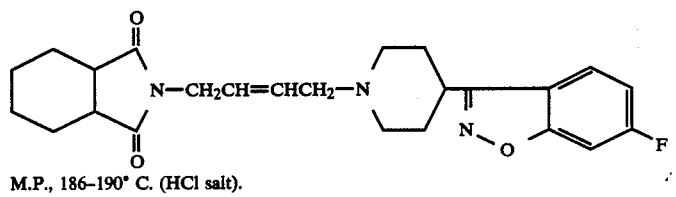

M.P., 186–190° C. (HCl salt).

Example 19

In the same manner as in Example 1, 2, 3 or 4, there was obtained N-[4-{4-(6-fluoro-1,2-benzisoxazol-3-yl)-

Example 20

In the same manner as in Example 1, 2, 3 or 4, there was obtained N-[2-{4-(6-fluoro-1,2-benzisoxazol-3-yl)-piperidinyl}ethyl]cyclohexane-1,2-dicarboximide of the following formula:

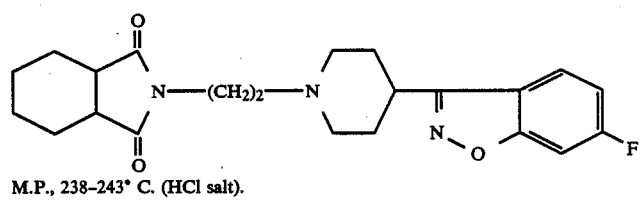

M.P., 238–243° C. (HCl salt).

Example 21

In the same manner as in Example 1, 2, 3 or 4, there was obtained N-[3-{4-(6-fluoro-1,2-benzisoxazol-3-yl)-piperidinyl}propyl]cyclohexane-1,2-dicarboximide of the following formula:

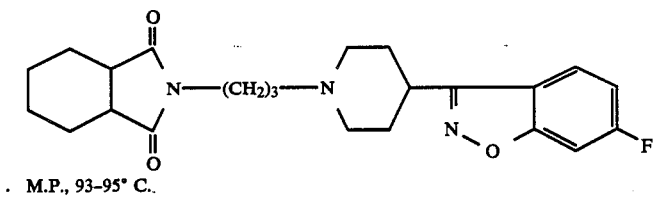

M.P., 93–95° C.

Example 22

In the same manner as in Example 1, 2, 3 or 4, there was obtained N-[5-{4-(6-fluoro-1,2-benzisoxazol-3-yl)-piperidinyl}pentyl]cyclohexane-1,2-dicarboximide of the following formula:

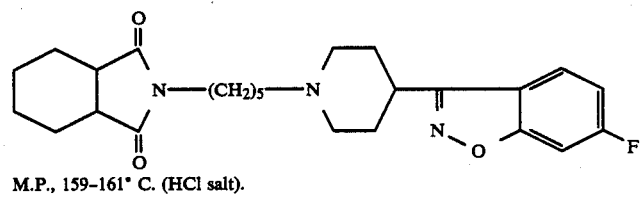

M.P., 159–161° C. (HCl salt).

Example 23

In the same manner as in Example 1, 2, 3 or 4, there was obtained N-[4{4-(6-fluoro-1,2-benzisoxazol-3-yl)-piperidinyl}-3-hydroxybutyl]bicyclo[2.2.1]heptane-2,3-diexo-carboximide of the following formula:

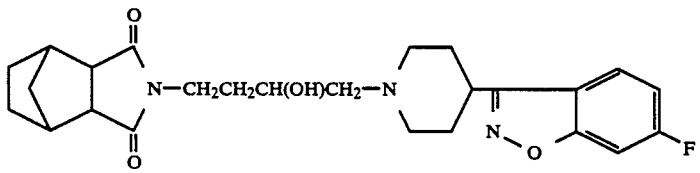

M.P., 243–247° C. (HCl salt).

Example 24

In the same manner as in Example 1, 2, 3 or 4, there was obtained N-[4-{4-(6-fluoro-1,2-benzisoxazol-3-yl)-piperidinyl}-2-hydroxybutyl]bicyclo[2.2.1]heptane-2,3-diexo-carboximide of the following formula:

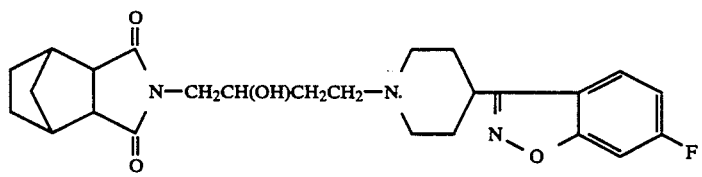

M.P., 223–224° C. (HCl salt).

Example 25

In the same manner as in Example 1, 2, 3 or 4, there was obtained N-[4-{4-(6-methyl-1,2-benzisoxazol-3-yl)-piperidinyl}butyl]cyclohexane-1,2-dicarboximide of the following formula:

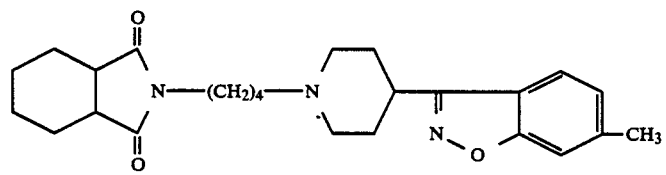

M.P., 199–200° C. (HCl salt).

Example 26

In the same manner as in Example 1, 2, 3 or 4, there was obtained N-[4-{4-(6-methyl-1,2-benzisoxazol-3-yl)-piperidinyl}butyl]bicyclo[2.2.1]heptane-2,3-di-exo-carboximide of the following formula:

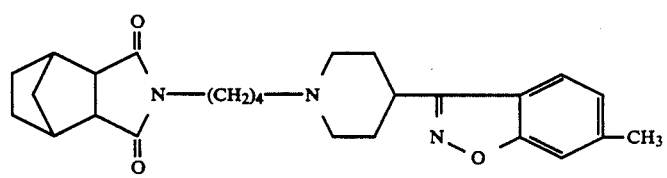

M.P., 226–227° C. (HCl salt).

Example 27

In the same manner as in Example 1, 2, 3 or 4, there was obtained N-[4{4-(6-chloro-1,2-benzisoxazol-3-yl)-piperidinyl}butyl]cyclohexane-1,2-dicarboximide of the following formula:

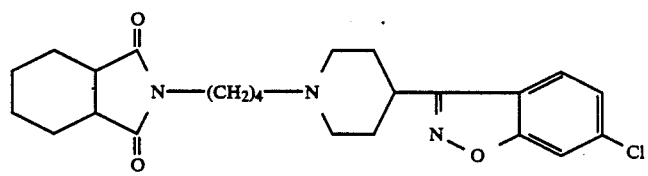

M.P., 217–218° C. (HCl salt).

Example 28

In the same manner as in Example 1, 2, 3 or 4, there was obtained N-[4-{4-(6-chloro-1,2-benzisoxazol-3-yl)-piperidinyl} butyl]bicyclo[2.2.1]heptane-2,3-di-exo-carboximide of the following formula:

M.P., 242–243° C. (HCl salt).

What is claimed is:

1. A compound of the formula:

(I)

wherein

A is a carbonyl group or a sulfonyl group;
B is either one of the formulas:

(in which $R_1$ and $R_2$ are each a hydrogen atom, or either one of them is a hydrogen atom and the other is a hydroxyl group, a $C_1$-$C_5$ alkyl group or a $C_2$-$C_6$ alkanoyloxy group, or $R_1$ and $R_2$ are combined together to represent an oxo group, E is a methylene group, an ethylene group or an oxygen atom and the full line accompanying a broken line (⇌) indicates a single bond or a double bond), (in which F is a methylene group or an ethylene group and $R_1$, $R_2$ and the full line accompanying a broken line (⇌) are each as defined above), (in which $R_3$, $R_4$, $R_5$, $R_6$, $R_7$ and $R_8$ are each a hydrogen atom or a $C_1$-$C_5$ alkyl group and $R_1$, $R_2$ and the full line accompanying a broken line (⇌) are each as defined above), or (in which $R_9$ and $R_{10}$ are each a $C_1$-$C_5$ alkyl group) when
A represents a carbonyl group,
or B is a 1,2-phenylene group when A represents a sulfonyl group;
W is a $C_1$-$C_6$ alkylene group, a $C_2$-$C_6$ alkenylene group, a $C_2$-$C_6$ alkynylene group or a $C_2$-$C_6$ alkylene group substituted with hydroxyl; and
G is a hydrogen atom, a $C_1$-$C_5$ alkyl group, a $C_1$-$C_5$ alkoxy group, a halogen atom or a hydroxyl group, or its pharmaceutically acceptable salt.

2. The compound according to claim 1, wherein A is a carbonyl group and B is a group of the formula:

(in which $R_1$ and $R_2$ are each as defined in claim 1), or its pharmaceutically acceptable salt.

3. The compound according to claim 1, wherein A is a carbonyl group and B is a group of the formula:

(in which F, $R_1$ and $R_2$ are each as defined in claim 1), or its pharmaceutically acceptable salt.

4. The compound according to claim 1, wherein A is a carbonyl group and B is a group of the formula:

(in which $R_3$, $R_4$, $R_5$, $R_6$, $R_7$ and $R_8$ are each as defined in claim 1), or its pharmaceutically acceptable salt.

5. The compound according to claim 1, wherein A is a carbonyl group and B is a group of the formula:

(in which $R_9$ and $R_{10}$ are each as defined in claim 1), or its pharmaceutically acceptable salt.

6. The compound according to claim 1, wherein A is a sulfonyl group and B is a 1,2-phenylene group, or its pharmaceutically acceptable salt.

7. The compound according to claim 1, wherein W is —(CH$_2$)$_4$—, —CH$_2$CH=CHCH$_2$—, —CH$_2$C≡CCH$_2$—, —CH$_2$CH(OH)CH$_2$CH$_2$— or —CH$_2$CH$_2$CH(OH)(CH$_2$)— and G is a hydrogen atom, a C$_1$–C$_5$ alkyl group, a C$_1$–C$_5$ alkoxy group, a halogen atom or a hydroxyl group, or its pharmaceutically acceptable salt.

8. The compound according to claim 1, which is the one representable by the formula:

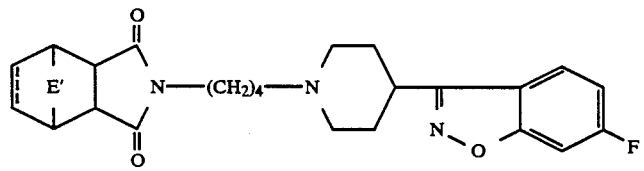

wherein E' is a methylene group or an ethylene group and the full line accompanying a broken line (—) is as defined in claim 1, or its pharmaceutically acceptable salt.

9. The compound according to claim 1, which is the one representable by the formula:

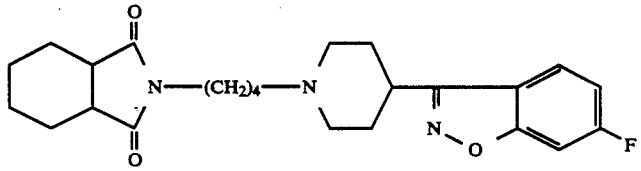

wherein the full line accompanying a broken line ( ) is as defined in claim 1, or its pharmaceutically acceptable salt.

10. A pharmaceutical composition for treatment of psychosis which comprises an active ingredient a pharmaceutically effective amount of the compound (I) or its pharmaceutically acceptable acid addition salt according to claim 1, and at least one pharmaceutically acceptable inert carrier or diluent.

11. A method for treatment of psychosis which comprises administering a pharmaceutically effective amount of the compound (I) or its pharmaceutically acceptable acid addition salt according to claim 1 to a human being in need thereof.

* * * * *